(12) United States Patent
Hoekstra et al.

(10) Patent No.: US 10,370,353 B2
(45) Date of Patent: Aug. 6, 2019

(54) ANTIFUNGAL COMPOUNDS AND PROCESSES FOR MAKING

(71) Applicant: Mycovia Pharmaceuticals, Inc., Durham, NC (US)

(72) Inventors: William J. Hoekstra, Durham, NC (US); David Dale Wirth, Oak Ridge, NC (US); Tracy Ehiwe, Cambridge (GB); Thierry Bonnaud, Cambridge (GB)

(73) Assignee: Mycovia Pharmaceuticals, Inc., Durham, NC (US)

( * ) Notice: Subject to any disclaimer, the term of this patent is extended or adjusted under 35 U.S.C. 154(b) by 0 days.

(21) Appl. No.: 15/835,991

(22) Filed: Dec. 8, 2017

(65) Prior Publication Data

US 2018/0319768 A1 Nov. 8, 2018

Related U.S. Application Data

(62) Division of application No. 15/317,006, filed as application No. PCT/US2016/022858 on Mar. 17, 2016, now Pat. No. 9,840,492.

(60) Provisional application No. 62/135,682, filed on Mar. 19, 2015.

(51) Int. Cl.
*C07D 401/06* (2006.01)

(52) U.S. Cl.
CPC .................. *C07D 401/06* (2013.01)

(58) Field of Classification Search
CPC .................................................. C07D 401/06
USPC ........................................................ 546/268.4
See application file for complete search history.

(56) References Cited

U.S. PATENT DOCUMENTS

2011/0306644 A1   12/2011   Hoekstra et al.

FOREIGN PATENT DOCUMENTS

| KR | 10-1128370 | 4/2012 |
| WO | WO2003/106461 | 12/2003 |
| WO | WO2007/052943 | 5/2007 |
| WO | WO2013/109998 | 7/2013 |
| WO | WO2013/110002 | 7/2013 |
| WO | WO2014/009921 | 1/2014 |

OTHER PUBLICATIONS

International Search Report and Written Opinion dated Sep. 2, 2016 in connection with PCT/US2016/022858 (V0286.70027W000).
Garvey et al., "VT-1161 dosed once daily or once weekly exhibits potent efficacy in treatment of dermatophytosis in a guinea pig model" Antimicrob Agents Chemother. Apr. 2015;59(4):1992-7. doi: 10.1128/AAC.04902-14. Epub Jan. 20, 2015.
Hoekstra et al., "Design and optimization of highly-selective fungal CYP51 inhibitors", Bioorg Med Chem Lett. Aug. 1, 2014;24(15):3455-8. doi: 10.1016/j.bmcl.2014.05.068. Epub Jun. 9, 2014.

*Primary Examiner* — Patricia L Morris
(74) *Attorney, Agent, or Firm* — Brinks Gilson & Lione

(57) ABSTRACT

The present invention relates to polymorphic forms of compound 1 or 1a and processes for preparing compound 1 and 1a polymorphs, which are useful as antifungal agents. In particular, the invention seeks to provide a new methodology for preparing polymorphs of compound 1 and substituted derivatives thereof.

11 Claims, 7 Drawing Sheets

ANTIFUNGAL COMPOUNDS AND PROCESSES FOR MAKING

CROSS-REFERENCE TO RELATED APPLICATIONS

This application is a Divisional Application of U.S. application Ser. No. 15/317,006 filed Dec. 7, 2016, which is a U.S. National Phase Application under 35 U.S.C. § 371 of PCT International Application No. PCT/US2016/022858, filed Mar. 17, 2016, which claims the benefit and priority of U.S. Provisional Application No. 62/135,682, filed Mar. 19, 2015, the entire contents of the aforementioned applications are hereby incorporated herein by reference.

TECHNICAL FIELD

The present invention relates to polymorphic forms of compound 1 or 1a and processes for preparing compound 1 and 1a polymorphs, which are useful as an antifungal agents. In particular, the invention seeks to provide a new methodology for preparing polymorphs of compound 1 and substituted derivatives thereof.

BACKGROUND

It is well known that the crystalline polymorph form of a particular drug is often an important determinant of the drug's ease of preparation, stability, solubility, storage stability, ease of formulation and in vivo pharmacology. Polymorphic forms occur where the same composition of matter crystallizes in a different lattice arrangement resulting in different thermodynamic properties and stabilities specific to the particular polymorph form. In cases where two or more polymorph substances can be produced, it is desirable to have a method to prepare each of the polymorphs in pure form. In deciding which polymorph is preferable, the numerous properties of the polymorphs must be compared and the preferred polymorph chosen based on the many physical property variables. It is entirely possible for example that one polymorph form can be preferable in some circumstances where certain aspects such as ease of preparation, stability, etc. are deemed to be especially important. In other situations, for example, a different polymorph may be preferred for greater solubility and/or superior pharmacokinetics.

Because improved drug formulations, showing, for example, better bioavailability or better stability are consistently sought, there is an ongoing need for new or purer polymorphic forms of existing drug molecules. The various crystalline polymorphs of Compounds 1 or 1a described herein help meet these and other needs.

BRIEF SUMMARY OF THE INVENTION

The invention is directed toward polymorph forms of compounds 1 or 1a. The invention is also directed toward methods of synthesis of 1 or 1a. The methods can comprise the compounds herein.

One aspect of the invention relates to polymorph forms of compounds of formula 1 or 1a, or a pharmaceutically acceptable salt, hydrate, solvate, complex or prodrug thereof.

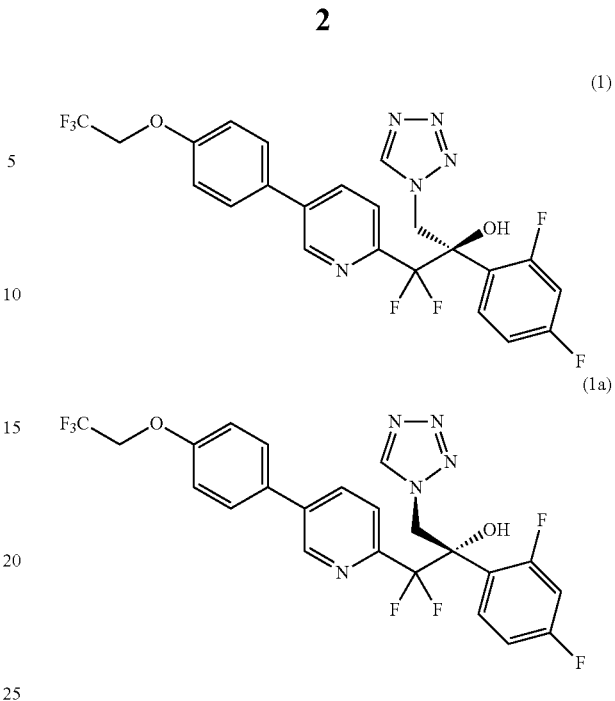

In another aspect, the invention is an anhydrous form of a compound of any of the formulae herein. In other aspects, the anhydrous form of a compound of any of the formulae herein is isolated. In other aspects, the anhydrous form of a compound of any of the formulae herein is isolated and has less than 2 weight % water therein (e.g., <1 wt. %, <0.5 wt. %, <0.25 wt. %, <0.1 wt. %). In other aspects, the anhydrous form of a compound of any of the formulae herein is isolated and has less than 750 ppm water therein (e.g., <500 ppm, <400 ppm, <300 ppm, <250 ppm, <200 ppm, <150 ppm, <100 ppm, <50 ppm).

In another aspect, the invention is a salt, hydrate, or solvate form of a compound of any of the formulae herein, having the physicochemical characteristics described herein.

The compounds herein include those wherein the compound is identified as attaining affinity, at least in part, for a metalloenzyme by formation of one or more of the following types of chemical interactions or bonds to a metal: sigma bonds, covalent bonds, coordinate-covalent bonds, ionic bonds, pi bonds, delta bonds, or backbonding interactions.

Compounds 1 and 1a are described in the art, including in U.S. Pat. No. 8,236,962 (incorporated by reference herein), as are methods of making them.

Methods for assessing metal-ligand binding interactions are known in the art as exemplified in references including, for example, "Principles of Bioinorganic Chemistry" by Lippard and Berg, University Science Books, (1994); "Mechanisms of Inorganic Reactions" by Basolo and Pearson John Wiley & Sons Inc; 2nd edition (September 1967); "Biological Inorganic Chemistry" by Ivano Bertini, Harry Gray, Ed Stiefel, Joan Valentine, University Science Books (2007); Xue et al. "Nature Chemical Biology", vol. 4, no. 2, 107-109 (2008).

In the following aspects, reference is made to the schemes and compounds herein, including the reagents and reaction conditions delineated herein. Other aspects include any of the compounds, reagents, transformations or methods thereof delineated in the examples herein (in whole or in part), including as embodiments with single elements (e.g., compounds or transformations) or embodiments including multiple elements (e.g., compounds or transformations).

In another aspect, the invention provides a method to prepare an anhydrous form of any compound of a formulae herein comprising placing a compound of a formulae herein in a solvent and recrystallizing and isolating the compound as an anhydrous form of the compound. In another aspect, the method further comprises: drying the resulting anhydrous compound; drying the resulting anhydrous compound under vacuum; drying the resulting anhydrous compound under vacuum at about 35° C. or higher (e.g., 40° C. or higher; 45° C. or higher; 50° C. or higher).

In aspects, the method above comprises: an organic solvent (e.g., ethers, ketones, esters, alcohols, amides, acetonitrile, and the like), an alcohol solvent (e.g., methanol, ethanol, 1-propanol, 2-propanol, butanol, and the like); two or more solvents (e.g., a combination of alcohols, a combination of an alcohol and a hydrocarbon, 2-propanol and n-hexane); or three or more solvents (e.g., a combination of three alcohols, a combination of two alcohols and a hydrocarbon). Solvents useful herein are known in the art.

In aspects, the method above comprises: an organic solvent (e.g., hydrocarbons, ethers, ketones, esters, amides, acetonitrile, and the like), an alcohol solvent (e.g., methanol, ethanol, 1-propanol, 2-propanol, butanol, and the like), or water; two or more solvents (e.g., a combination of an organic solvent and an alcohol; a combination of an alcohol and a hydrocarbon; 2-propanol and n-heptane); or three or more solvents. In another aspect, the method comprises a combination of solvents, wherein said combination contains <15% (w/w) total amount of water, methanol, and ethanol. In another aspect, the combination of solvents comprises an organic solvent (e.g., hexanes, heptanes, tert-butyl methyl ether, cyclohexane, toluene, anisole, xylene, cyclohexanone, methyl-tetrahydrofuran, dimethylformamide, N-methylpyrrolidinone) and an alcohol (e.g., methanol, ethanol, 1-propanol, 2-propanol, butanol), wherein said combination contains <X % (w/w) total amount of water, methanol, and ethanol. In another aspect, the combination of solvents is 2-propanol and an organic solvent. In another aspect, the combination of solvents is an alcohol and n-heptane, wherein said combination contains <X % (w/w) total amount of water, methanol, and ethanol. In another aspect, the combination of solvents is 2-propanol and n-heptane. Solvents useful herein are known in the art.

In another aspect, the invention is an anhydrous form of a compound of any of the formulae herein, made by a process described herein.

Another aspect of the invention relates to a process for preparing a polymorph form of compound of formula 1 or 1a, or a pharmaceutically acceptable salt, hydrate, solvate, complex or prodrug thereof.

In another aspect, the crystallization solvent or crystallization solvent mixture from any of the embodiments presented herein is ethyl acetate, isopropyl acetate, ethanol, methanol, or acetonitrile, or combinations thereof.

In another aspect, the crystallization co-solvent or crystallization co-solvent mixture from any of the embodiments presented herein is pentane, methyl t-butylether, hexane, heptane, or toluene, or combinations thereof.

In another aspect, any of the embodiments presented herein may comprise repeating the enantio-enrichment step(s) until desired level of enantio-enrichment is attained. In another aspect, any of the embodiments presented herein may comprise repeating the enantio-enrichment step(s) and/or purification steps until desired level of enantio-enrichment and/or purification is attained.

In other aspects, the invention provides a compound of any of the formulae herein, wherein the compound inhibits (or is identified to inhibit) lanosterol demethylase (CYP51). In another aspect, the invention provides a pharmaceutical composition comprising a compound of any formulae herein and a pharmaceutically acceptable carrier.

In other aspects, the invention provides a method of modulating metalloenzyme activity in a subject, comprising contacting the subject with a compound of any formulae herein, in an amount and under conditions sufficient to modulate metalloenzyme activity.

In one aspect, the invention provides a method of treating a subject suffering from or susceptible to a metalloenzyme-related disorder or disease, comprising administering to the subject an effective amount of a compound or pharmaceutical composition of any formulae herein.

In another aspect, the invention provides a method of treating a subject suffering from or susceptible to a metalloenzyme-related disorder or disease, wherein the subject has been identified as in need of treatment for a metalloenzyme-related disorder or disease, comprising administering to said subject in need thereof, an effective amount of a compound or pharmaceutical composition of any formulae herein, such that said subject is treated for said disorder.

In another aspect, the invention provides a method of treating a subject suffering from or susceptible to a metalloenzyme-mediated disorder or disease, wherein the subject has been identified as in need of treatment for a metalloenzyme-mediated disorder or disease, comprising administering to said subject in need thereof, an effective amount of a compound or pharmaceutical composition of any formulae herein, such that metalloenzyme activity in said subject is modulated (e.g., down regulated, inhibited). In another aspect, the compounds delineated herein preferentially target cancer cells over nontransformed cells.

DETAILED DESCRIPTION

Definitions

Figure 1:
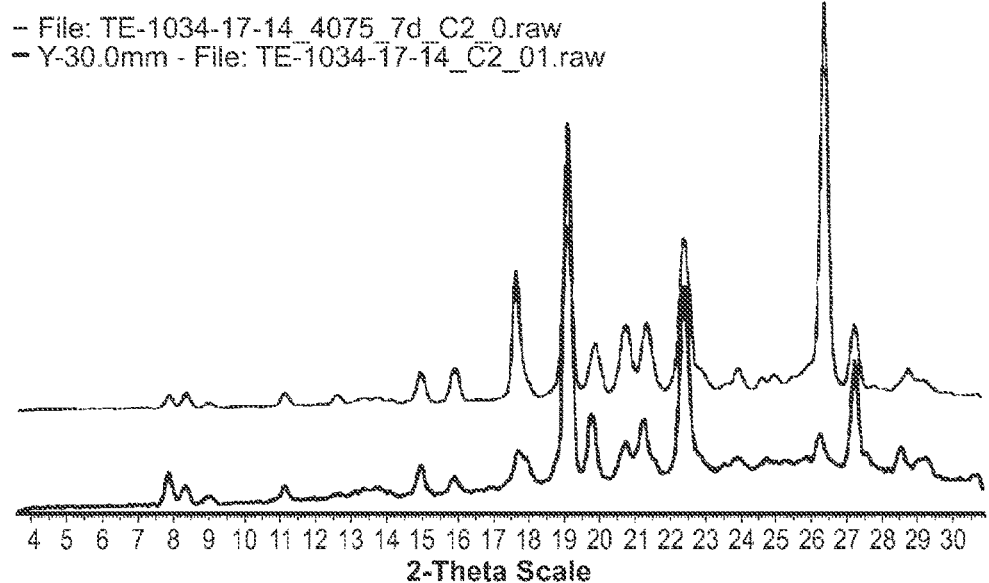
FIG. 1: depicts a XRPD pattern of an anhydrous form of compound 1.
Figure 2:
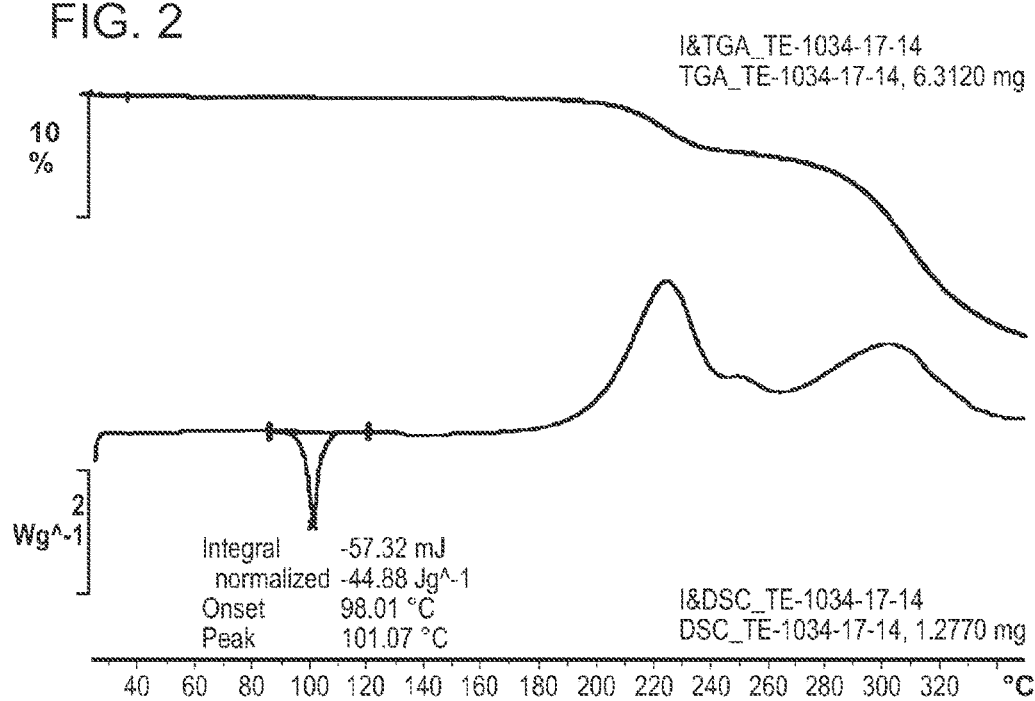
FIG. 2: depicts a thermal analysis pattern of an anhydrous form of compound 1.
Figure 3:
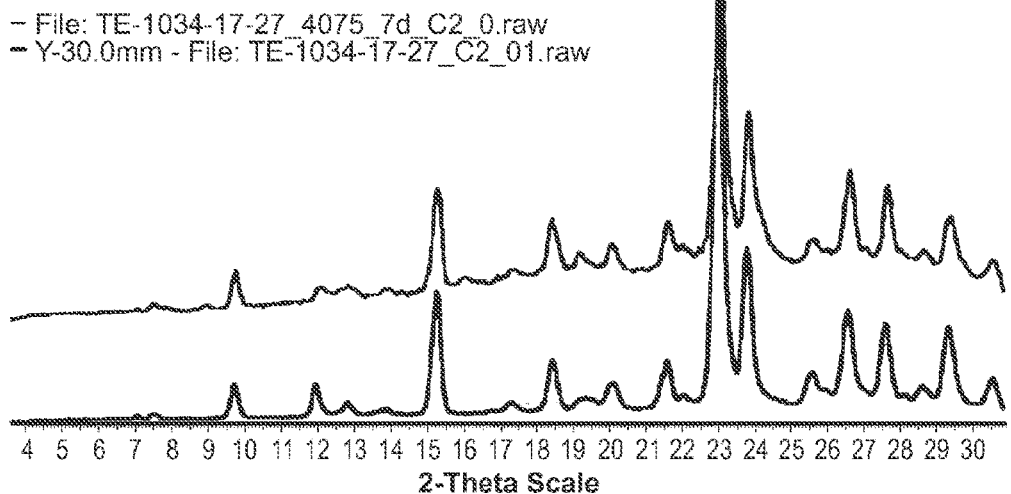
FIG. 3: depicts a XRPD pattern of an ethanol solvate form of compound 1.
Figure 4:
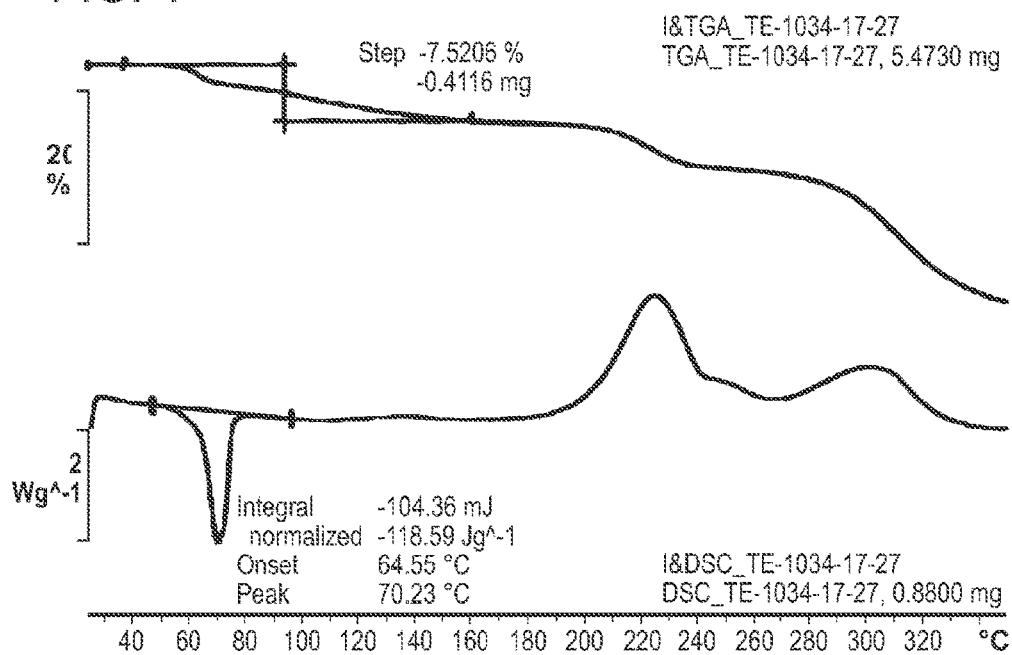
FIG. 4: depicts a thermal analysis pattern of an ethanol solvate form of compound 1.

The term "chiral" refers to molecules which have the property of non-superimposability of the mirror image partner, while the term "achiral" refers to molecules which are superimposable on their mirror image partner.

The term "diastereomers" refers to stereoisomers with two or more centers of dissymmetry and whose molecules are not mirror images of one another.

The term "enantiomers" refers to two stereoisomers of a compound which are non-superimposable mirror images of one another. An equimolar mixture of two enantiomers is called a "racemic mixture" or a "racemate."

The term "isomers" or "stereoisomers" refers to compounds which have identical chemical constitution, but differ with regard to the arrangement of the atoms or groups in space.

The term "prodrug" includes compounds with moieties which can be metabolized in vivo. Generally, the prodrugs are metabolized in vivo by esterases or by other mechanisms to active drugs. Examples of prodrugs and their uses are well known in the art (see e.g., Berge et al. (1977) "Pharmaceutical Salts", *J. Pharm. Sci.* 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkylamino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters. Prodrugs which are converted to active forms through other mechanisms in vivo are also included. In aspects, the compounds of the invention are prodrugs of any of the formulae herein.

The term "subject" refers to animals such as mammals, including, but not limited to, primates (e.g., humans), cows, sheep, goats, horses, dogs, cats, rabbits, rats, mice and the like. In certain embodiments, the subject is a human.

The terms "a," "an," and "the" refer to "one or more" when used in this application, including the claims. Thus, for example, reference to "a sample" includes a plurality of samples, unless the context clearly is to the contrary (e.g., a plurality of samples), and so forth. Throughout this specification and the claims, the words "comprise," "comprises," and "comprising" are used in a non-exclusive sense, except where the context requires otherwise.

As used herein, the term "about," when referring to a value is meant to encompass variations of, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Use of the word "inhibitor" herein is meant to mean a molecule that exhibits activity for inhibiting a metalloenzyme. By "inhibit" herein is meant to decrease the activity of metalloenzyme, as compared to the activity of metalloenzyme in the absence of the inhibitor. In some embodiments, the term "inhibit" means a decrease in metalloenzyme activity of at least about 5%, at least about 10%, at least about 20%, at least about 25%, at least about 50%, at least about 60%, at least about 70%, at least about 80%, at least about 90%, or at least about 95%. In other embodiments, inhibit means a decrease in metalloenzyme activity of about 5% to about 25%, about 25% to about 50%, about 50% to about 75%, or about 75% to 100%. In some embodiments, inhibit means a decrease in metalloenzyme activity of about 95% to 100%, e.g., a decrease in activity of 95%, 96%, 97%, 98%, 99%, or 100%. Such decreases can be measured using a variety of techniques that would be recognizable by one of skill in the art. Particular assays for measuring individual activity are described below.

Furthermore the compounds of the invention include olefins having either geometry: "Z" refers to what is referred to as a "cis" (same side) configuration whereas "E" refers to what is referred to as a "trans" (opposite side) configuration. With respect to the nomenclature of a chiral center, the terms "D" and "L" configuration are as defined by the IUPAC Recommendations. As to the use of the terms, diastereomer, racemate, epimer and enantiomer, these will be used in their normal context to describe the stereochemistry of preparations.

As used herein, the term "alkyl" refers to a straight-chained or branched hydrocarbon group containing 1 to 12 carbon atoms. The term "lower alkyl" refers to a $C_1$-$C_6$ alkyl chain. Examples of alkyl groups include methyl, ethyl, n-propyl, isopropyl, tert-butyl, and n-pentyl. Alkyl groups may be optionally substituted with one or more substituents.

The term "alkenyl" refers to an unsaturated hydrocarbon chain that may be a straight chain or branched chain, containing 2 to 12 carbon atoms and at least one carbon-carbon double bond. Alkenyl groups may be optionally substituted with one or more substituents.

The term "alkynyl" refers to an unsaturated hydrocarbon chain that may be a straight chain or branched chain, containing the 2 to 12 carbon atoms and at least one carbon-carbon triple bond. Alkynyl groups may be optionally substituted with one or more substituents.

The $sp^2$ or sp carbons of an alkenyl group and an alkynyl group, respectively, may optionally be the point of attachment of the alkenyl or alkynyl groups.

The term "alkoxy" refers to an —O-alkyl radical.

As used herein, the term "halogen", "hal" or "halo" means —F, —Cl, —Br or —I.

The term "haloalkoxy" refers to an —O-alkyl radical that is substituted by one or more halo substituents. Examples of haloalkoxy groups include trifluoromethoxy, and 2,2,2-trifluoroethoxy.

The term "cycloalkyl" refers to a hydrocarbon 3-8 membered monocyclic or 7-14 membered bicyclic ring system having at least one saturated ring or having at least one non-aromatic ring, wherein the non-aromatic ring may have some degree of unsaturation. Cycloalkyl groups may be optionally substituted with one or more substituents. In one embodiment, 0, 1, 2, 3, or 4 atoms of each ring of a cycloalkyl group may be substituted by a substituent. Representative examples of cycloalkyl group include cyclopropyl, cyclopentyl, cyclohexyl, cyclobutyl, cycloheptyl, cyclopentenyl, cyclopentadienyl, cyclohexenyl, cyclohexadienyl, and the like.

The term "aryl" refers to a hydrocarbon monocyclic, bicyclic or tricyclic aromatic ring system. Aryl groups may be optionally substituted with one or more substituents. In one embodiment, 0, 1, 2, 3, 4, 5 or 6 atoms of each ring of an aryl group may be substituted by a substituent. Examples of aryl groups include phenyl, naphthyl, anthracenyl, fluorenyl, indenyl, azulenyl, and the like.

The term "heteroaryl" refers to an aromatic 5-8 membered monocyclic, 8-12 membered bicyclic, or 11-14 membered tricyclic ring system having 1-4 ring heteroatoms if monocyclic, 1-6 heteroatoms if bicyclic, or 1-9 heteroatoms if tricyclic, said heteroatoms selected from O, N, or S, and the remainder ring atoms being carbon (with appropriate hydrogen atoms unless otherwise indicated). Heteroaryl groups may be optionally substituted with one or more substituents. In one embodiment, 0, 1, 2, 3, or 4 atoms of each ring of a heteroaryl group may be substituted by a substituent. Examples of heteroaryl groups include pyridyl, furanyl, thienyl, pyrrolyl, oxazolyl, oxadiazolyl, imidazolyl thiazolyl, isoxazolyl, quinolinyl, pyrazolyl, isothiazolyl, pyridazinyl, pyrimidinyl, pyrazinyl, triazinyl, isoquinolinyl, indazolyl, and the like.

The term "nitrogen-containing heteroaryl" refers to a heteroaryl group having 1-4 ring nitrogen heteroatoms if monocyclic, 1-6 ring nitrogen heteroatoms if bicyclic, or 1-9 ring nitrogen heteroatoms if tricyclic.

The term "heterocycloalkyl" refers to a nonaromatic 3-8 membered monocyclic, 7-12 membered bicyclic, or 10-14 membered tricyclic ring system comprising 1-3 heteroatoms if monocyclic, 1-6 heteroatoms if bicyclic, or 1-9 heteroatoms if tricyclic, said heteroatoms selected from O, N, S, B, P or Si, wherein the nonaromatic ring system is completely saturated. Heterocycloalkyl groups may be optionally substituted with one or more substituents. In one embodiment, 0, 1, 2, 3, or 4 atoms of each ring of a heterocycloalkyl group may be substituted by a substituent. Representative heterocycloalkyl groups include piperidinyl, piperazinyl, tetrahydropyranyl, morpholinyl, thiomorpholinyl, 1,3-dioxolane, tetrahydrofuranyl, tetrahydrothienyl, thienyl, and the like.

The term "alkylamino" refers to an amino substituent which is further substituted with one or two alkyl groups. The term "aminoalkyl" refers to an alkyl substituent which is further substituted with one or more amino groups. The term "hydroxyalkyl" or "hydroxylalkyl" refers to an alkyl substituent which is further substituted with one or more hydroxyl groups. The alkyl or aryl portion of alkylamino, aminoalkyl, mercaptoalkyl, hydroxyalkyl, mercaptoalkoxy, sulfonylalkyl, sulfonylaryl, alkylcarbonyl, and alkylcarbonylalkyl may be optionally substituted with one or more substituents.

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions.

Alkylating agents are any reagent that is capable of effecting the alkylation of the functional group at issue (e.g., oxygen atom of an alcohol, nitrogen atom of an amino group). Alkylating agents are known in the art, including in the references cited herein, and include alkyl halides (e.g., methyl iodide, benzyl bromide or chloride), alkyl sulfates (e.g., methyl sulfate), or other alkyl group-leaving group combinations known in the art. Leaving groups are any stable species that can detach from a molecule during a reaction (e.g., elimination reaction, substitution reaction) and are known in the art, including in the references cited herein, and include halides (e.g., I—, Cl—, Br—, F—), hydroxy, alkoxy (e.g., —OMe, —O-t-Bu), acyloxy anions (e.g., —OAc, —OC(O)CF3), sulfonates (e.g., mesyl, tosyl), acetamides (e.g., —NHC(O)Me), carbamates (e.g., N(Me)C(O)Ot-Bu), phosphonates (e.g., —OP(O)(OEt)2), water or alcohols (protic conditions), and the like.

In certain embodiments, substituents on any group (such as, for example, alkyl, alkenyl, alkynyl, aryl, aralkyl, heteroaryl, heteroaralkyl, cycloalkyl, heterocycloalkyl) can be at any atom of that group, wherein any group that can be substituted (such as, for example, alkyl, alkenyl, alkynyl, aryl, aralkyl, heteroaryl, heteroaralkyl, cycloalkyl, heterocycloalkyl) can be optionally substituted with one or more substituents (which may be the same or different), each replacing a hydrogen atom. Examples of suitable substituents include, but are not limited to alkyl, alkenyl, alkynyl, cycloalkyl, heterocycloalkyl, aralkyl, heteroaralkyl, aryl, heteroaryl, halogen, haloalkyl, cyano, nitro, alkoxy, aryloxy, hydroxyl, hydroxyalkyl, oxo (i.e., carbonyl), carboxyl, formyl, alkylcarbonyl, alkylcarbonylalkyl, alkoxycarbonyl, alkylcarbonyloxy, aryloxycarbonyl, heteroaryloxy, heteroaryloxycarbonyl, thio, mercapto, mercaptoalkyl, arylsulfonyl, amino, aminoalkyl, dialkylamino, alkylcarbonylamino, alkylaminocarbonyl, alkoxycarbonylamino, alkylamino, arylamino, diarylamino, alkylcarbonyl, or arylamino-substituted aryl; arylalkylamino, aralkylaminocarbonyl, amido, alkylaminosulfonyl, arylaminosulfonyl, dialkylaminosulfonyl, alkyl sulfonylamino, arylsulfonylamino, imino, carbamido, carbamyl, thioureido, thiocyanato, sulfoamido, sulfonylalkyl, sulfonylaryl, mercaptoalkoxy, N-hydroxyamidinyl, or N'-aryl, N"-hydroxyamidinyl.

Compounds of the invention can be made by means known in the art of organic synthesis. Methods for optimizing reaction conditions, if necessary minimizing competing by products, are known in the art. Reaction optimization and scale up may advantageously utilize high speed parallel synthesis equipment and computer controlled microreactors (e.g., *Design and Optimization in Organic Synthesis*, 2nd Edition, Carlson R, Ed., 2005; Elsevier Science Ltd.; Jahnisch, K et al, *Angew. Chem. Int. Ed. Engl.* 2004 43: 406; and references therein). Additional reaction schemes and protocols may be determined by the skilled artesian by use of commercially available structure searchable database software, for instance, SciFinder® (CAS division of the American Chemical Society) and CrossFire Beilstein® (Elsevier MDL), or by appropriate keyword searching using an internet search engine such as Google® or keyword databases such as the US Patent and Trademark Office text database. The invention includes the intermediate compounds used in making the compounds of the formulae herein as well as methods of making such compounds and intermediates, including without limitation those as specifically described in the examples herein.

The compounds herein may also contain linkages (e.g., carbon-carbon bonds) wherein bond rotation is restricted about that particular linkage, e.g. restriction resulting from the presence of a ring or double bond. Accordingly, all cis/trans and E/Z isomers are expressly included in the present invention. The compounds herein may also be represented in multiple tautomeric forms, in such instances, the invention expressly includes all tautomeric forms of the compounds described herein, even though only a single tautomeric form may be represented. All such isomeric forms of such compounds herein are expressly included in the present invention. All crystal forms and polymorphs of the compounds described herein are expressly included in the present invention. Also embodied are extracts and fractions comprising compounds of the invention. The term isomers is intended to include diastereoisomers, enantiomers, regioisomers, structural isomers, rotational isomers, tautomers, and the like. For compounds which contain one or more stereogenic centers, e.g., chiral compounds, the methods of the invention may be carried out with an enantiomerically enriched compound, a racemate, or a mixture of diastereomers.

Preferred enantiomerically enriched compounds have an enantiomeric excess of 50% or more, more preferably the compound has an enantiomeric excess of 60%, 70%, 80%, 90%, 95%, 98%, or 99% or more. In preferred embodiments, only one enantiomer or diastereomer of a chiral compound of the invention is administered to cells or a subject.

Pharmaceutical Compositions

In one aspect, the invention provides a pharmaceutical composition comprising a compound of any formulae herein and a pharmaceutically acceptable carrier.

In another embodiment, the invention provides a pharmaceutical composition further comprising an additional therapeutic agent. In a further embodiment, the additional therapeutic agent is an anti-cancer agent, antifungal agent, cardiovascular agent, antiinflammatory agent, chemotherapeutic agent, an anti-angiogenesis agent, cytotoxic agent, an anti-proliferation agent, metabolic disease agent, ophthalmologic disease agent, central nervous system (CNS) disease agent, urologic disease agent, or gastrointestinal disease agent.

In one aspect, the invention provides a kit comprising an effective amount of a compound of any formulae herein, in unit dosage form, together with instructions for administering the compound to a subject suffering from or susceptible to a metalloenzyme-mediated disease or disorder, including cancer, solid tumor, cardiovascular disease, inflammatory disease, infectious disease. In other embodiments the disease, disorder or symptom thereof is metabolic disease, ophthalmologic disease, central nervous system (CNS) disease, urologic disease, or gastrointestinal disease.

The term "pharmaceutically acceptable salts" or "pharmaceutically acceptable carrier" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydroiodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see e.g., Berge et al., *Journal of Pharmaceutical Science* 66:1-19 (1977)).

Certain specific compounds of the present invention contain both basic and acidic functionalities that allow the compounds to be converted into either base or acid addition salts. Other pharmaceutically acceptable carriers known to those of skill in the art are suitable for the present invention.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

The invention also provides a pharmaceutical composition, comprising an effective amount a compound described herein and a pharmaceutically acceptable carrier. In an embodiment, compound is administered to the subject using a pharmaceutically-acceptable formulation, e.g., a pharmaceutically-acceptable formulation that provides sustained delivery of the compound to a subject for at least 12 hours, 24 hours, 36 hours, 48 hours, one week, two weeks, three weeks, or four weeks after the pharmaceutically-acceptable formulation is administered to the subject.

Actual dosage levels and time course of administration of the active ingredients in the pharmaceutical compositions of this invention may be varied so as to obtain an amount of the active ingredient which is effective to achieve the desired therapeutic response for a particular patient, composition, and mode of administration, without being toxic (or unacceptably toxic) to the patient.

In use, at least one compound according to the present invention is administered in a pharmaceutically effective amount to a subject in need thereof in a pharmaceutical carrier by intravenous, intramuscular, subcutaneous, or intracerebro ventricular injection or by oral administration or topical application. In accordance with the present invention, a compound of the invention may be administered alone or in conjunction with a second, different therapeutic. By "in conjunction with" is meant together, substantially simultaneously or sequentially. In one embodiment, a compound of the invention is administered acutely. The compound of the invention may therefore be administered for a short course of treatment, such as for about 1 day to about 1 week. In another embodiment, the compound of the invention may be administered over a longer period of time to ameliorate chronic disorders, such as, for example, for about one week to several months depending upon the condition to be treated.

By "pharmaceutically effective amount" as used herein is meant an amount of a compound of the invention, high enough to significantly positively modify the condition to be treated but low enough to avoid serious side effects (at a reasonable benefit/risk ratio), within the scope of sound medical judgment. A pharmaceutically effective amount of a compound of the invention will vary with the particular goal to be achieved, the age and physical condition of the patient being treated, the severity of the underlying disease, the duration of treatment, the nature of concurrent therapy and the specific compound employed. For example, a therapeutically effective amount of a compound of the invention administered to a child or a neonate will be reduced proportionately in accordance with sound medical judgment. The effective amount of a compound of the invention will thus be the minimum amount which will provide the desired effect.

A decided practical advantage of the present invention is that the compound may be administered in a convenient manner such as by intravenous, intramuscular, subcutaneous, oral or intra-cerebroventricular injection routes or by topical application, such as in creams or gels. Depending on the route of administration, the active ingredients which comprise a compound of the invention may be required to be coated in a material to protect the compound from the action of enzymes, acids and other natural conditions which may inactivate the compound. In order to administer a compound of the invention by other than parenteral administration, the compound can be coated by, or administered with, a material to prevent inactivation.

The compound may be administered parenterally or intraperitoneally. Dispersions can also be prepared, for example, in glycerol, liquid polyethylene glycols, and mixtures thereof, and in oils.

Some examples of substances which can serve as pharmaceutical carriers are sugars, such as lactose, glucose and sucrose; starches such as corn starch and potato starch; cellulose and its derivatives such as sodium carboxymethylcellulose, ethylcellulose and cellulose acetates; powdered tragancanth; malt; gelatin; talc; stearic acids; magnesium stearate; calcium sulfate; vegetable oils, such as peanut oils, cotton seed oil, sesame oil, olive oil, corn oil and oil of theobroma; polyols such as propylene glycol, glycerine, sorbitol, manitol, and polyethylene glycol; agar; alginic acids; pyrogen-free water; isotonic saline; and phosphate buffer solution; skim milk powder; as well as other non-toxic compatible substances used in pharmaceutical formulations such as Vitamin C, estrogen and echinacea, for example. Wetting agents and lubricants such as sodium lauryl sulfate, as well as coloring agents, flavoring agents, lubricants, excipients, tableting agents, stabilizers, anti-oxidants and preservatives, can also be present. Solubilizing agents, including for example, Cremaphore and beta-cyclodextrins, can also used in the pharmaceutical compositions herein.

Pharmaceutical compositions comprising the active compounds of the presently disclosed subject matter (or prodrugs thereof) can be manufactured by means of conventional mixing, dissolving, granulating, dragee-making levigating, emulsifying, encapsulating, entrapping or lyophilization processes. The compositions can be formulated in conventional manner using one or more physiologically acceptable carriers, diluents, excipients or auxiliaries which facilitate processing of the active compounds into preparations which can be used pharmaceutically.

Pharmaceutical compositions of the presently disclosed subject matter can take a form suitable for virtually any mode of administration, including, for example, topical, ocular, oral, buccal, systemic, nasal, injection, transdermal, rectal, vaginal, and the like, or a form suitable for administration by inhalation or insufflation.

For topical administration, the active compound(s) or prodrug(s) can be formulated as solutions, gels, ointments, creams, suspensions, and the like.

Systemic formulations include those designed for administration by injection, e.g., subcutaneous, intravenous, intramuscular, intrathecal or intraperitoneal injection, as well as those designed for transdermal, transmucosal, oral, or pulmonary administration.

Useful injectable preparations include sterile suspensions, solutions or emulsions of the active compound(s) in aqueous or oily vehicles. The compositions also can contain formulating agents, such as suspending, stabilizing and/or dispersing agent. The formulations for injection can be presented in unit dosage form (e.g., in ampules or in multidose containers) and can contain added preservatives.

Alternatively, the injectable formulation can be provided in powder form for reconstitution with a suitable vehicle, including but not limited to sterile pyrogen free water, buffer, dextrose solution, and the like, before use. To this end, the active compound(s) can be dried by any art-known technique, such as lyophilization, and reconstituted prior to use.

For transmucosal administration, penetrants appropriate to the barrier to be permeated are used in the formulation. Such penetrants are known in the art.

For oral administration, the pharmaceutical compositions can take the form of, for example, lozenges, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets can be coated by methods well known in the art with, for example, sugars or enteric coatings.

Liquid preparations for oral administration can take the form of, for example, elixirs, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non aqueous vehicles (e.g., almond oil, oily esters, ethyl alcohol or fractionated vegetable oils); and preservatives (e.g., methyl or propyl p-hydroxybenzoates or sorbic acid). The preparations also can contain buffer salts, preservatives, flavoring, coloring and sweetening agents as appropriate.

Preparations for oral administration can be suitably formulated to give controlled release of the active compound or prodrug, as is well known.

For buccal administration, the compositions can take the form of tablets or lozenges formulated in a conventional manner.

For rectal and vaginal routes of administration, the active compound(s) can be formulated as solutions (for retention enemas), suppositories, or ointments containing conventional suppository bases, such as cocoa butter or other glycerides.

For nasal administration or administration by inhalation or insufflation, the active compound(s) or prodrug(s) can be conveniently delivered in the form of an aerosol spray from pressurized packs or a nebulizer with the use of a suitable propellant, e.g., dichlorodifluoromethane, trichlorofluoromethane, dichlorotetrafluoroethane, fluorocarbons, carbon dioxide or other suitable gas. In the case of a pressurized aerosol, the dosage unit can be determined by providing a valve to deliver a metered amount. Capsules and cartridges for use in an inhaler or insufflator (for example capsules and cartridges comprised of gelatin) can be formulated containing a powder mix of the compound and a suitable powder base such as lactose or starch.

A specific example of an aqueous suspension formulation suitable for nasal administration using commercially-available nasal spray devices includes the following ingredients: active compound or prodrug (0.5-20 mg/mL); benzalkonium chloride (0.1-0.2 mg/mL); polysorbate 80 (TWEEN® 80; 0.5-5 mg/mL); carboxymethylcellulose sodium or microcrystalline cellulose (1-15 mg/mL); phenylethanol (1-4 mg/mL); and dextrose (20-50 mg/mL). The pH of the final suspension can be adjusted to range from about pH 5 to pH 7, with a pH of about pH 5.5 being typical.

For prolonged delivery, the active compound(s) or prodrug(s) can be formulated as a depot preparation for administration by implantation or intramuscular injection. The active ingredient can be formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch which slowly releases the active compound(s) for percutaneous absorption can be used. To this end, permeation enhancers can be used to facilitate transdermal penetration of the active compound(s). Suitable transdermal patches are described in for example, U.S. Pat. Nos. 5,407,713; 5,352,456; 5,332,213; 5,336,168; 5,290,561; 5,254,346; 5,164,189; 5,163,899; 5,088,977; 5,087,240; 5,008,110; and 4,921,475, each of which is incorporated herein by reference in its entirety.

Alternatively, other pharmaceutical delivery systems can be employed. Liposomes and emulsions are well-known examples of delivery vehicles that can be used to deliver active compound(s) or prodrug(s). Certain organic solvents such as dimethylsulfoxide (DMSO) also can be employed.

The pharmaceutical compositions can, if desired, be presented in a pack or dispenser device which can contain one or more unit dosage forms containing the active compound(s). The pack can, for example, comprise metal or plastic foil, such as a blister pack. The pack or dispenser device can be accompanied by instructions for administration.

The active compound(s) or prodrug(s) of the presently disclosed subject matter, or compositions thereof, will generally be used in an amount effective to achieve the intended result, for example in an amount effective to treat or prevent the particular disease being treated. The compound(s) can be administered therapeutically to achieve therapeutic benefit or prophylactically to achieve prophylactic benefit. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient can still be afflicted with the underlying disorder. For example, administration of a compound to a patient suffering from an allergy provides therapeutic benefit not only when the underlying allergic response is eradicated or ameliorated, but also when the patient reports a decrease in the severity or duration of the symptoms associated with the allergy following exposure to the allergen. As another example, therapeutic benefit in the context of asthma includes an improvement in respiration following the onset of an asthmatic attack, or a reduction in the frequency or severity of asthmatic episodes. Therapeutic benefit also includes halting or slowing the progression of the disease, regardless of whether improvement is realized.

For prophylactic administration, the compound can be administered to a patient at risk of developing one of the previously described diseases. A patient at risk of developing a disease can be a patient having characteristics placing the patient in a designated group of at risk patients, as defined by an appropriate medical professional or group. A patient at risk may also be a patient that is commonly or routinely in a setting where development of the underlying disease that may be treated by administration of a metalloenzyme inhibitor according to the invention could occur. In other words, the at risk patient is one who is commonly or routinely exposed to the disease or illness causing conditions or may be acutely exposed for a limited time. Alternatively, prophylactic administration can be applied to avoid the onset of symptoms in a patient diagnosed with the underlying disorder.

The amount of compound administered will depend upon a variety of factors, including, for example, the particular indication being treated, the mode of administration, whether the desired benefit is prophylactic or therapeutic, the severity of the indication being treated and the age and weight of the patient, the bioavailability of the particular active compound, and the like. Determination of an effective dosage is well within the capabilities of those skilled in the art.

Effective dosages can be estimated initially from in vitro assays. For example, an initial dosage for use in animals can be formulated to achieve a circulating blood or serum concentration of active compound that is at or above an IC50 of the particular compound as measured in as in vitro assay, such as the in vitro fungal MIC or MFC and other in vitro assays described in the Examples section. Calculating dosages to achieve such circulating blood or serum concentrations taking into account the bioavailability of the particular compound is well within the capabilities of skilled artisans. For guidance, see Fingl & Woodbury, "General Principles," In: Goodman and Gilman's *The Pharmaceutical Basis of Therapeutics*, Chapter 1, pp. 1-46, latest edition, Pagamonon Press, and the references cited therein, which are incorporated herein by reference.

Initial dosages also can be estimated from in vivo data, such as animal models. Animal models useful for testing the efficacy of compounds to treat or prevent the various diseases described above are well-known in the art.

Dosage amounts will typically be in the range of from about 0.0001 or 0.001 or 0.01 mg/kg/day to about 100 mg/kg/day, but can be higher or lower, depending upon, among other factors, the activity of the compound, its bioavailability, the mode of administration, and various factors discussed above. Dosage amount and interval can be adjusted individually to provide plasma levels of the compound(s) which are sufficient to maintain therapeutic or prophylactic effect. In cases of local administration or selective uptake, such as local topical administration, the effective local concentration of active compound(s) cannot be related to plasma concentration. Skilled artisans will be able to optimize effective local dosages without undue experimentation.

The compound(s) can be administered once per day, a few or several times per day, or even multiple times per day, depending upon, among other things, the indication being treated and the judgment of the prescribing physician.

Preferably, the compound(s) will provide therapeutic or prophylactic benefit without causing substantial toxicity. Toxicity of the compound(s) can be determined using standard pharmaceutical procedures. The dose ratio between toxic and therapeutic (or prophylactic) effect is the therapeutic index. Compounds(s) that exhibit high therapeutic indices are preferred.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof. The recitation of an embodiment herein includes that embodiment as any single embodiment or in combination with any other embodiments or portions thereof.

Another object of the present invention is the use of a compound as described herein (e.g., of any formulae herein) in the manufacture of a medicament for use in the treatment of a metalloenzyme-mediated disorder or disease. Another object of the present invention is the use of a compound as described herein (e.g., of any formulae herein) for use in the treatment of a metalloenzyme-mediated disorder or disease. Another object of the present invention is the use of a compound as described herein (e.g., of any formulae herein) in the manufacture of an agricultural composition for use in the treatment or prevention of a metalloenzyme-mediated disorder or disease in agricultural or agrarian settings.

Agricultural Applications

The compounds and compositions herein can be used in methods of modulating metalloenzyme activity in a microorganism on a plant comprising contacting a compound (or composition) herein with the plant (e.g., seed, seedling, grass, weed, grain). The compounds and compositions herein can be used to treat a plant, field or other agricultural area (e.g., as herbicides, pesticides, growth regulators, etc.) by administering the compound or composition (e.g., contacting, applying, spraying, atomizing, dusting, etc.) to the subject plant, field or other agricultural area. The administration can be either pre- or post-emergence. The administration can be either as a treatment or preventative regimen.

The present invention will now be demonstrated using specific examples that are not to be construed as limiting.

EXAMPLES

General Experimental Procedures

X-Ray Powder Diffraction patterns were collected on a Bruker AXS C2 GADDS diffractometer using Cu Kα radiation (40 kV, 40 mA), automated XYZ stage, laser video microscope for auto-sample positioning and a HiStar 2-dimensional area detector. X-ray optics consists of a single Göbel multilayer mirror coupled with a pinhole collimator of 0.3 mm. A weekly performance check is carried out using a certified standard NIST 1976 Corundum (flat plate). The beam divergence, i.e. the effective size of the X-ray beam on the sample, was approximately 4 mm. A Θ-Θ continuous scan mode was employed with a sample-detector distance of 20 cm which gives an effective 2θ range of 3.2°-29.7°. Typically the sample would be exposed to the X-ray beam for 120 seconds. The software used for data collection was GADDS for XP/2000 4.1.43 and the data were analysed and presented using Diffrac Plus EVA v13.0.0.2 or v15.0.0.0. Samples run under ambient conditions were prepared as flat plate specimens using powder as received without grinding. Approximately 1-2 mg of the sample was lightly pressed on a glass slide to obtain a flat surface. Samples run under non-ambient conditions were mounted on a silicon wafer with heat-conducting compound. The sample was then heated to the appropriate temperature at 30° C./min and subsequently held isothermally for 1 minute before data collection was initiated.

X-Ray Powder Diffraction patterns were also collected on a Bruker D8 diffractometer using Cu Kα radiation (40 kV, 40 mA), 0-20 goniometer, and divergence of V4 and receiving slits, a Ge monochromator and a Lynxeye detector. The instrument is performance checked using a certified Corundum standard (NIST 1976). The software used for data collection was Diffrac Plus XRD Commander v2.6.1 and the data were analysed and presented using Diffrac Plus EVA v13.0.0.2 or v15.0.0.0. Samples were run under ambient conditions as flat plate specimens using powder as received. The sample was gently packed into a cavity cut into polished, zero-background (510) silicon wafer. The sample was rotated in its own plane during analysis. The details of the data collection are: Angular range: 2 to 42° 2Θ; Step size: 0.05° 2 Θ; Collection time: 0.5 s/step.

Single crystal X-ray diffraction data (SCXRD) were collected on an Oxford Diffraction Supernova Dual Source, Cu at Zero, Atlas CCD diffractometer equipped with an Oxford Cryosystems Cobra cooling device. The data was collected using CuKα radiation. Structures were typically solved using either the SHELXS or SHELXD programs and refined with the SHELXL program as part of the Bruker AXS SHELXTL suite (V6.10). Unless otherwise stated, hydrogen atoms attached to carbon were placed geometrically and allowed to refine with a riding isotropic displacement parameter. Hydrogen atoms attached to a heteroatom were located in a difference Fourier synthesis and were allowed to refine freely with an isotropic displacement parameter.

Differential Scanning calorimetry (Modulated temperature DSC) was carried out using an underlying heating rate of 2° C./min and temperature modulation parameters of ±0.636° C. or ±1.272° C. (amplitude) every 60 seconds (period). The instrument control software was Advantage for Q Series v2.8.0.394 and Thermal Advantage v5.2.6 and the data were analysed using Universal Analysis v4.7A or v4.4A.

DSC data was also collected on a Mettler DSC 823E equipped with a 34 position auto-sampler. The instrument was calibrated for energy and temperature using certified indium. Typically 0.5-3 mg of each sample, in a pin-holed aluminium pan, was heated at 10° C./min from 25° C. to 350° C. A nitrogen purge at 50 mL/min was maintained over the sample. The instrument control and data analysis software was STARe v9.20.

NMR spectra were collected on a Bruker 400 MHz instrument equipped with an auto-sampler and controlled by a DRX400 console. Automated experiments were acquired using ICON-NMR v4.0.7 running with Topspin v1.3 using the standard Bruker loaded experiments. For non-routine spectroscopy, data were acquired through the use of Topspin alone. Samples were prepared in deuterated chloroform (CDCl3), unless otherwise stated. Off-line analysis was carried out using Topspin v1.3 or ACD SpecManager v12.5.

Fourier Transform—Infra-red (FTIR) Data were collected on a Perkin-Elmer Spectrum One fitted with a universal Attenuated Total Reflectance (ATR) sampling accessory. The data were collected and analysed using Spectrum v10.0.1 software.

Thermo-gravimetric analysis (TGA) data were collected on a Mettler TGA/SDTA 851e equipped with a 34 position auto-sampler. The instrument was temperature calibrated using certified indium. Typically 2-8 mg of each sample was loaded onto a pre-weighed aluminium crucible and was heated at 10° C./min from ambient temperature to 350° C. A nitrogen purge at 50 mL/min was maintained over the sample. The instrument control and data analysis software was STARe v9.20.

The water content of each sample was measured by Karl Fischer titration (KF) on a Metrohm 874 Oven Sample Processor at 150° C. with 851 Titrano Coulometer using Hydranal Coulomat AG oven reagent and nitrogen purge. Weighed solid samples were introduced into a sealed sample vial. Approximately 10 mg of sample was used per titration and duplicate determinations were made.

Gravimetric Vapor Sorption (GVS) isotherms were obtained using a SMS DVS Intrinsic moisture sorption analyser, controlled by DVS Intrinsic Control software v1.0.1.2 (or v 1.0.1.3). The sample temperature was maintained at 25° C. by the instrument controls. The humidity was controlled by mixing streams of dry and wet nitrogen, with a total flow rate of 200 mL/min. The relative humidity was measured by a calibrated Rotronic probe (dynamic range of 1.0-100% RH), located near the sample. The weight change, (mass relaxation) of the sample as a function of % RH was constantly monitored by the microbalance (accuracy ±0.005 mg). Typically 5-20 mg of sample was placed in a tared mesh stainless steel basket under ambient conditions. The sample was loaded and unloaded at 40% RH and 25° C. (typical room conditions). A moisture sorption isotherm was performed as outlined below (2 scans giving 1 complete cycle). The standard isotherm was performed at 25° C. at 10% RH intervals over a 0-90% RH range. Data analysis was undertaken in Microsoft Excel using DVS Analysis Suite v6.2 (or 6.1 or 6.0).

Method Parameters for SMS DVS Intrinsic Experiments

| Parameters | Values |
| --- | --- |
| Adsorption - Scan 1 | 40-90 |
| Desorption/Adsorption - Scan 2 | 90-0, 0-40 |
| Intervals (% RH) | 10 |
| Number of Scans | 4 |
| Flow rate (ml/min) | 200 |
| Temperature (° C.) | 25 |
| Stability (° C./min) | 0.2 |
| Sorption Time (hours) | 6 hour time out |

The sample was recovered after completion of the isotherm and re-analysed by XRPD.

Definitions of variables in the structures in schemes herein are commensurate with those of corresponding positions in the formulae delineated herein.

Synthesis of 1 or 1a

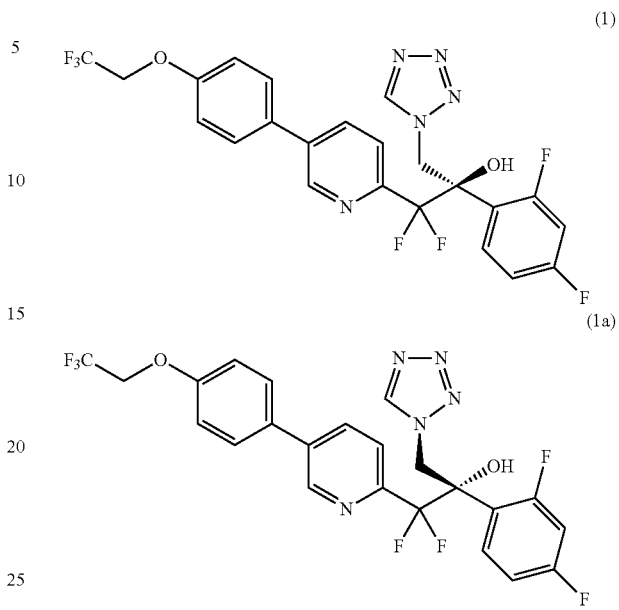

Example 1

Preparation of Compound 1 X-Hydrate

Compound 1 and its preparation are described in the art, including in U.S. Pat. No. 8,236,962 (incorporated by reference herein). Compound 1 can then be partitioned between ethanol and water to afford Compound 1 X-hydrate.

Example 2

Compound 1 Anhydrous Form Recrystallization

Compound 1 X-hydrate (29.1 g, 28.0 g contained 1) was suspended in 2-propanol (150 mL) and heated to 56° C. The solution was filtered through a 0.45 μm Nylon membrane with 2-propanol rinses. The combined filtrate was concentrated to 96.5 g of a light amber solution. The solution was transferred to a 1-L flask equipped with overhead stirring, thermocouple and addition funnel, using 2-propanol (30 mL total) to complete the transfer. The combined solution contained about 116 mL 2-propanol.

The solution was heated to 50° C. and n-heptane (234 mL) was added over 22 minutes. The resulting hazy mixture was seeded with 1 anhydrous form. After about 1 hour a good suspension had formed. Additional n-heptane (230 mL) was added over 48 minutes. Some granular material separated but most of the suspension was a finely divided pale beige solid. After about ½ hour at 50° C. the suspension was cooled at 10° C./h to room temperature and stirred overnight. The product was collected at 22° C. on a vacuum filter and washed with 1:4 (v/v) 2-PrOH/n-heptane (2×50 mL). After drying on the filter for 1-2 hours the weight of product was 25.5 g. The material was homogenized in a stainless steel blender to pulverize and blend the more granular solid component. The resulting pale beige powder (25.37 g) was dried in a vacuum oven at 50° C. The dry weight was 25.34 g. The residual 2-propanol and n-heptane were estimated at <0.05 wt % each by $^1$H NMR analysis. The yield was 90.5% after correcting the X-hydrate for solvent and water content. Residual Pd was 21 ppm. The water content was 209 ppm by KF titration. The melting point was 100.7° C. by DSC analysis.

TABLE 1

Data for the isolated and dried Compound 1 - X-hydrate and anhydrous forms

| Form | Yield (%) | M.P. (° C.) | Pd (ppm) | Purity (A %) | Chiral (A %) | H2O (wt %) | Residual Solvent (wt %) |
|---|---|---|---|---|---|---|---|
| X-Hydrate | 91.0 | 65 | 48 | 99.4 | NA | 2.16% | Ethanol - 1.7 wt % |
| Anhydrous | 90.5 | 101 | 21 | 99.8 | >99.9 | 209 ppm | 2-PrOH, heptane <0.1 wt % |

M.P. by DSC;
Pd by ICP;
Purity by the API HPLC method;
Chiral purity by HPLC;
water content by KF titration;
residual solvent estimated from $^1$H NMR.

TABLE 2

Characterisation Data for Compounds 1 (X-hydrate) and 1 (anhydrous)

| Technique | | X-hydrate 1 | Anhydrous 1 |
|---|---|---|---|
| XRPD | | Crystalline (Pattern 1) | Crystalline (anhydrous) |
| XRPD stability post 2 weeks at | 40° C. & 75% RH 25° C. & 97% RH | No change in crystalline form No change in crystalline form | No change in crystalline form No change in crystalline form |
| $^{1H}$NMR | | Consistent with 1 structure (0.2 mol of EtOH) | Consistent with 1 structure (0.02 mol of heptane) |
| Thermal | DSC | 62° C. (ΔH = −99 J/g) | Melt onset ~99° C. (ΔH = −37 J/g) |
| | TGA | 4.2% (40° C.-130° C.) Decomposition onset at ~190° C. | Decomposition onset at ~190° C. |
| HPLC | | 99.88% by area | 99.89% by area |
| PLM | | Needle like crystals particle size >100 μm | Needle like crystals and agglomerates particle size range from 5 μm-100 μm |
| GVS | | 0.59% w/w water uptake at 90% RH. No sample hysteresis | 0.14% w/w water uptake at 90% RH. No sample hysteresis |
| XRPD post GVS | | No form change after GVS experiment | No form change after GVS experiment |
| KF | | 2.4% w/w H$_2$O | Not obtained |
| Solubility | | <0.001 mg/ml pH of saturated solution = 8.6 | <0.001 mg/ml pH of saturated solution = 8.7 |
| FT-IR | | Spectral Pattern 1 Charcteristic bands/cm$^{-1}$: 3499, 3378, 3213, 3172 1612, 1598, 1588, 1522, 1502 931, 903, 875, 855, 828, 816 | Spectral Pattern 2 Charcteristic bands/cm$^{-1}$: 3162 1610, 1518, 1501 927, 858, 841, 829, 812 |

TABLE 3

Single Crystal Structure of 1 Anhydrous Form

| | |
|---|---|
| Molecular formula | C$_{23}$H$_{16}$F$_7$N$_5$O$_2$ |
| Molecular weight | 527.41 |
| Crystal system | Monoclinic |
| Space group | P2(1) a 10.9345(6) Å, α 90°, b 8.3118(5) Å, β 97.286(5)°, c 24.5678(14) Å, γ 90° |
| V | 2214.8(2) Å$^3$ |
| Z | 4 |
| D$_c$ | 1.582 g · cm$^{-3}$ |
| μ | 1.271 mm$^{-1}$ |
| Source, λ | Cu-Kα, 1.54178 Å |
| F(000) | 1072 |
| T | 100(2) K |
| Crystal | Colourless plate, 0.3 × 0.2 × 0.08 mm |
| Data truncated to | 0.80 Å |
| θmax | 74.49° |
| Completeness | 99.5% |
| Reflections | 23372 |
| Unique reflections | 8807 |
| Rint | 0.0327 |

The structure solution of Compound 1 anhydrous form was obtained by direct methods, full-matrix least-squares refinement on F$^2$ with weighting w$^{-1}$=σ$^2$(F$_o^2$)+(0.0474P)$^2$+ (0.3258P), where P=(F$_o^2$+2F$_c^2$)/3, anisotropic displacement parameters, empirical absorption correction using spherical harmonics, implemented in SCALE3 ABSPACK scaling algorithm. Final wR$^2$={Σ[w (F$_o^2$−F$_c^2$)$^2$]/Σ[w (F$_o^2$)$^2$]$^{1/2}$}=0.0877 for all data, conventional R1=0.0343 on F values of 8390 reflections with F$_o$>4a(F$_o$), S=1.051 for all data and 675 parameters. Final Δ/a (max) 0.001, Δ/a (mean), 0.000. Final difference map between +0.311 and −0.344 e Å$^{-3}$.

Figure 9:
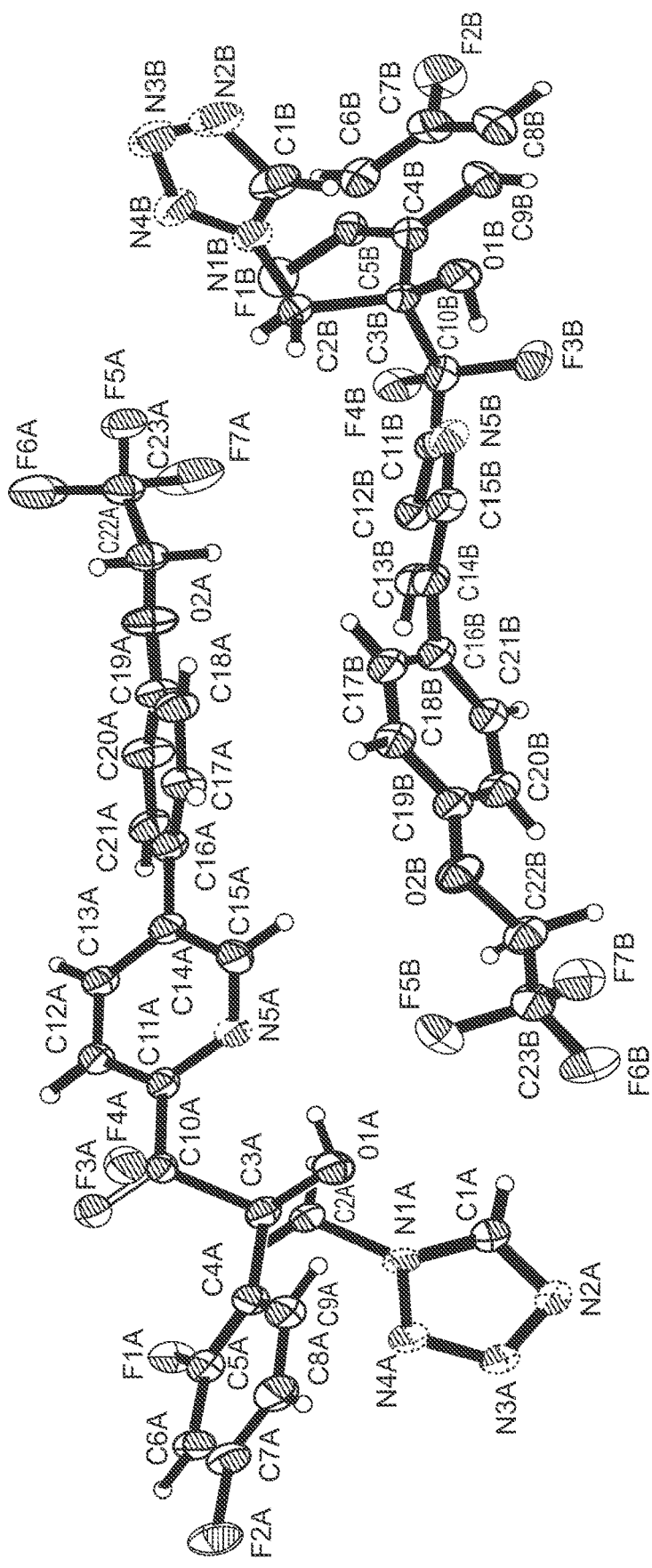
FIG. 9: depicts a view of the crystal structure asymmetric unit of the anhydrous form of Compound 1. Two molecules of Compound 1 are in the asymmetric unit.

FIG. 9 shows a view of two molecules of Compound 1 in the asymmetric unit of the anhydrous form. Anisotropic atomic displacement ellipsoids for the non-hydrogen atoms are shown at the 50% probability level. Hydrogen atoms are displayed with an arbitrarily small radius. The absolute configuration of the molecules has been determined to be R.

Example 3

Compound 1 Ethanol Solvate Recrystallization

Compound 1 X-hydrate (50 mg) was suspended in ~40 volumes of 15% H$_2$O/EtOH. The suspension was then placed in an incubation chamber for maturation. The maturation protocol involved treating the suspension to a two-temperature cycle of 50° C./ambient temperature at 8 hours per cycle for 3 days with constant agitation. After maturation, the suspension was cooled in a fridge at 4° C. for up to 2 days to encourage the formation of crystals. Then, the solvent was removed at RT and the sample was vacuum dried at 30° C.-35° C. for up to 1 day. Suitable crystals formed on cooling were harvested and characterized.

TABLE 4

Single Crystal Structure of 1 Ethanol solvate

| | |
|---|---|
| Molecular formula | $C_{25}H_{22}F_7N_5O_3$ |
| Molecular weight | 573.48 |
| Crystal system | Orthorhombic |
| Space group | P2(1)2(1)2(1)  a  7.4595(3) Å, α  90°, |
| | b  14.4651(6) Å, β  90°, |
| | c  22.6496(8) Å, γ  90° |
| V | 2443.95(17) Å$^3$ |
| Z | 4 |
| $D_c$ | 1.559 g · cm$^{-3}$ |
| μ | 1.232 mm$^{-1}$ |
| Source, λ | Cu-Kα 1.54178 Å |
| F(000) | 1176 |
| T | 100(2) K |
| Crystal | Colourless columnar, 0.25 × 0.05 × 0.05 mm |
| Data truncated to | 0.80 Å |
| θmax | 74.44° |
| Completeness | 99.3% |
| Reflections | 12874 |
| Unique reflections | 4872 |
| Rint | 0.0264 |

The structure solution of Compound 1 ethanol solvate was obtained by direct methods, full-matrix least-squares refinement on $F^2$ with weighting $w^{-1}=\sigma^2(F_o^2)+(0.0450P)^2+(0.5000P)$, where $P=(F_o^2+2F_c^2)/3$, anisotropic displacement parameters, empirical absorption correction using spherical harmonics, implemented in SCALE3 ABSPACK scaling algorithm. Final $wR^2=\{\Sigma[w(F_o^2-F_c^2)^2]/\Sigma[w(F_o^2)^2]\}^{1/2}=0.0777$ for all data, conventional R1=0.0272 on F values of 4591 reflections with $F_o>4\sigma(F_o)$, S=1.006 for all data and 370 parameters. Final Δ/σ (max) 0.000, Δ/σ (mean), 0.000. Final difference map between +0.217 and −0.199 e Å$^{-3}$.

Figure 10:
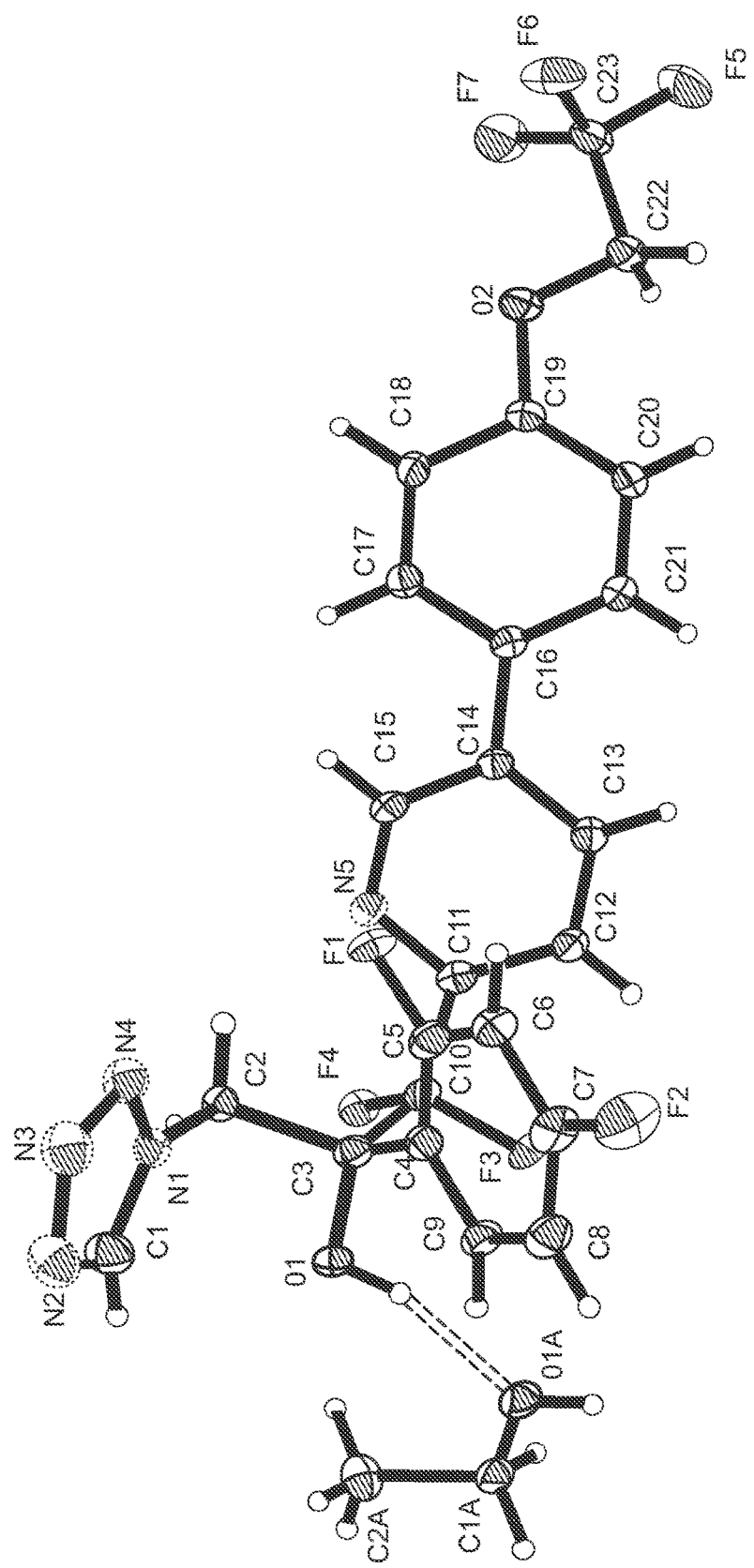
FIG. 10: depicts a view of the crystal structure asymmetric unit of the ethanol solvate of Compound 1.

FIG. 10 shows a view of the asymmetric unit of the ethanol solvate from the crystal structure. Anisotropic atomic displacement ellipsoids for the non-hydrogen atoms are shown at the 50% probability level. Hydrogen atoms are displayed with an arbitrarily small radius. The asymmetric unit shows stoichiometry of 1:1 for solvent of crystallisation to Compound 1.

Example 4

Compound 1 1.5 Hydrate Recrystallization

Compound 1 X-hydrate (50 mg) was suspended in ~40 volumes of 15% H$_2$O/IPA. The suspension was then placed in an incubation chamber for maturation. The maturation protocol involved treating the suspension to a two-temperature cycle of 50° C./ambient temperature at 8 hours per cycle for 3 days with constant agitation. After maturation, the suspension was cooled in a fridge at 4° C. for up to 2 days to encourage the formation of crystals. Then, the solvent was removed at RT and the sample was vacuum dried at 30° C.-35° C. for up to 1 day. Suitable crystals formed on cooling were harvested and characterized.

TABLE 5

Single Crystal Structure of 1 1.5 Hydrate

| | |
|---|---|
| Molecular formula | $C_{23}H_{18}F_7N_5O_{3.50}$ |
| Molecular weight | 553.42 |
| Crystal system | Monoclinic |

TABLE 5-continued

Single Crystal Structure of 1 1.5 Hydrate

| | |
|---|---|
| Space group | C2  a  22.409(3) Å, α  90°, |
| | b  7.5646(8) Å, β  103.372(15)°, |
| | c  13.979(2) Å, γ  90° |
| V | 2305.4(5) Å$^3$ |
| Z | 4 |
| $D_c$ | 1.595 g · cm$^{-3}$ |
| μ | 1.3 mm$^{-1}$ |
| Source, λ | Cu-Kα 1.54178 Å |
| F(000) | 1128 |
| T | 100(2) K |
| Crystal | Colourless columnar, 0.7 × 0.5 × 0.3 mm |
| Data truncated to | 0.80 Å |
| θmax | 58.93° |
| Completeness | 98.6% |
| Reflections | 3736 |
| Unique reflections | 2214 |
| Rint | 0.0454 |

The structure solution of Compound 1 1.5 hydrate was obtained by direct methods, full-matrix least-squares refinement on $F^2$ with weighting $w^{-1}=\sigma^2(F_o^2)+(0.1269P)^2+(0.0000P)$, where $P=(F_o^2+2F_c^2)/3$, anisotropic displacement parameters, empirical absorption correction using spherical harmonics, implemented in SCALE3 ABSPACK scaling algorithm. Final $wR^2=\{\Sigma[w(F_o^2-F_c^2)^2]/\Sigma[w(F_o^2)^2]\}^{1/2}=0.1574$ for all data, conventional R1=0.0668 on F values of 2106 reflections with $F_o>4\sigma(F_o)$, S=1.106 for all data and 361 parameters. Final Δ/σ (max) 0.000, Δ/σ (mean), 0.000. Final difference map between +0.439 and −0.598 e Å$^{-3}$.

Figure 11:
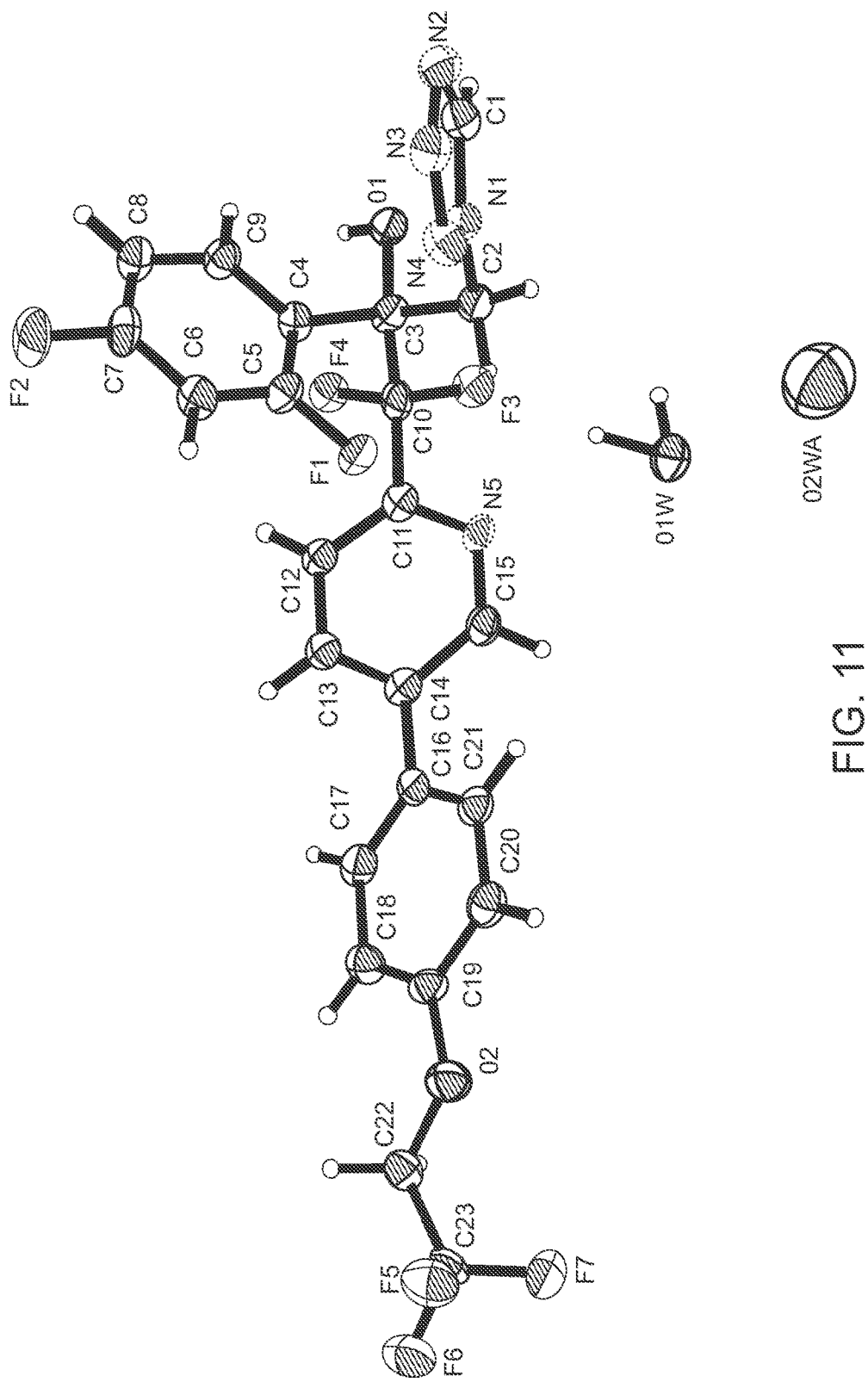
FIG. 11: depicts a view of the crystal structure asymmetric unit of the 1.5 hydrate of Compound 1.

FIG. 11 shows a view of the asymmetric unit of the 1.5 hydrate from the crystal structure. Anisotropic atomic displacement ellipsoids for the non-hydrogen atoms are shown at the 50% probability level. Hydrogen atoms are displayed with an arbitrarily small radius. The asymmetric unit shows stoichiometry of 1.5:1 for water to Compound 1.

Example 5

Human Pharmacokinetic Comparison of Compound 1 X-Hydrate and Compound 1 Anhydrous Form Table 6 compares human multiple-dose pharmacokinetic (PK) parameters between dosing with Compound 1 X-hydrate and Compound 1 Anhydrous form. Compound 1 X-hydrate was dosed at 600 mg twice daily (bid) for three days followed by dosing at 300 mg once daily (qd) for 10 days. Compound 1 Anhydrous form was dosed at 300 mg qd for 14 days. Despite the higher initial dosing amount and frequency (i.e., 600 mg bid) of Compound 1 X-hydrate, Compound 1 Anhydrous form surprisingly displayed higher maximal concentration ($C_{max}$) and higher area-under-the-curve (AUC) than Compound 1 X-hydrate.

TABLE 6

Comparison of Multiple Dose PK between Compound 1 X-Hydrate and Compound 1 Anhydrous Polymorph

| Test Article | Dose Regimen | $C_{max}$ (ng/mL) | $T_{max}$ (h) | $AUC_{0-8\,h}$ (ngh/mL) |
|---|---|---|---|---|
| Compound 1 X-Hydrate | 600 mg bid loading dose for 3 days, then 300 mg qd maintenance for 10 days | 2520 | 5 | 17600 |
| Compound 1 Anhydrous | 300 mg qd for 14 days | 4693 | 5 | 35653 |

Further characterization of the various polymorph forms of compound 1 are detailed in the accompanying figures.

INCORPORATION BY REFERENCE

The contents of all references (including literature references, issued patents, published patent applications, and co-pending patent applications) cited throughout this application are hereby expressly incorporated herein in their entireties by reference.

EQUIVALENTS

Those skilled in the art will recognize, or be able to ascertain using no more than routine experimentation, many equivalents of the specific embodiments of the invention described herein. Such equivalents are intended with be encompassed by the following claims.

Figure 5:
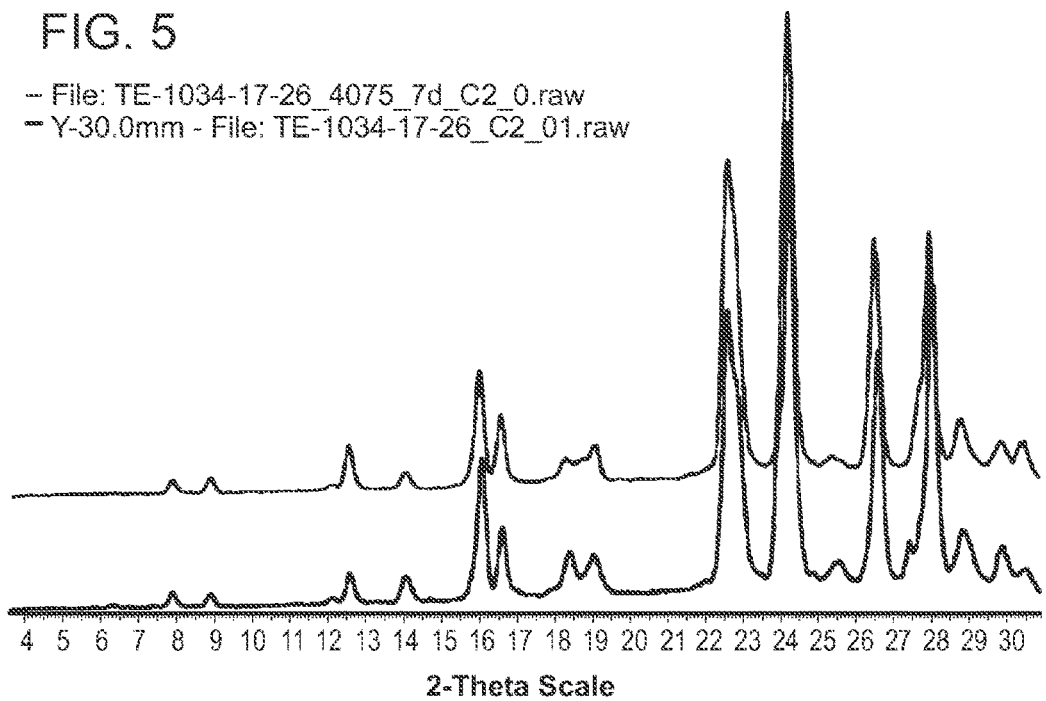
FIG. 5: depicts a XRPD pattern of a 1.5 hydrate form of compound 1.
Figure 6:
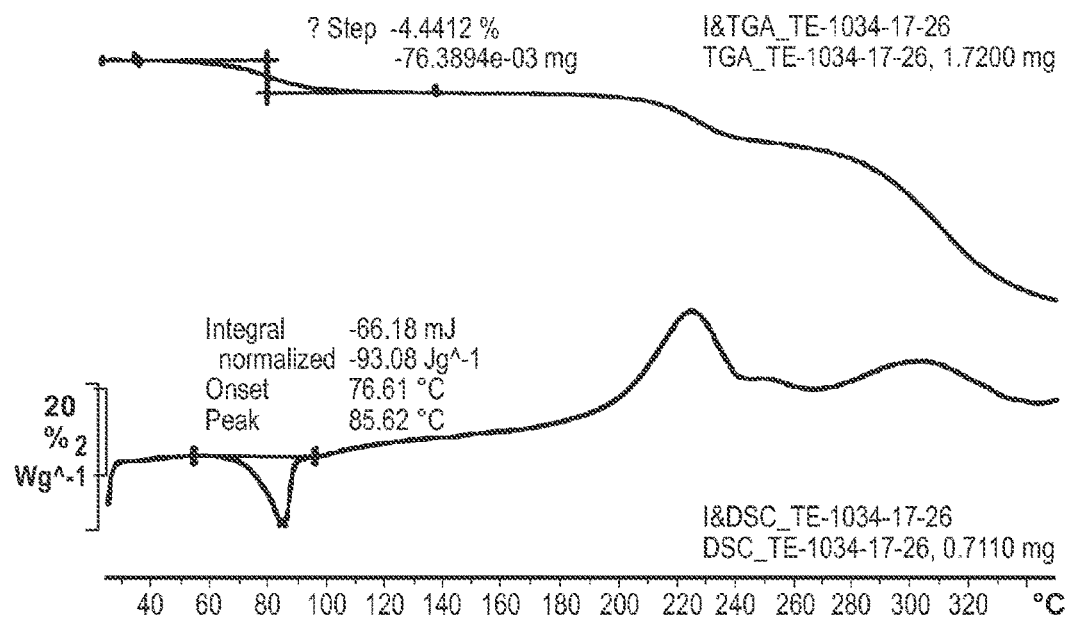
FIG. 6: depicts a thermal analysis pattern of a 1.5 hydrate form of compound 1.
Figure 7:
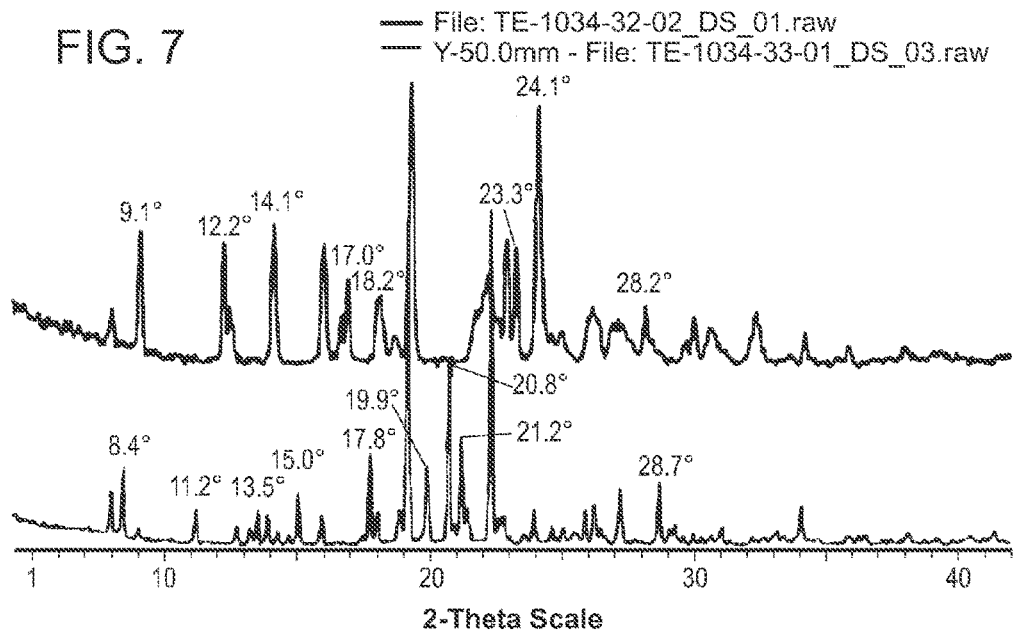
FIG. 7: depicts XRPD patterns of X-hydrate (upper) and anhydrous (lower) forms of compound 1.
Figure 8:
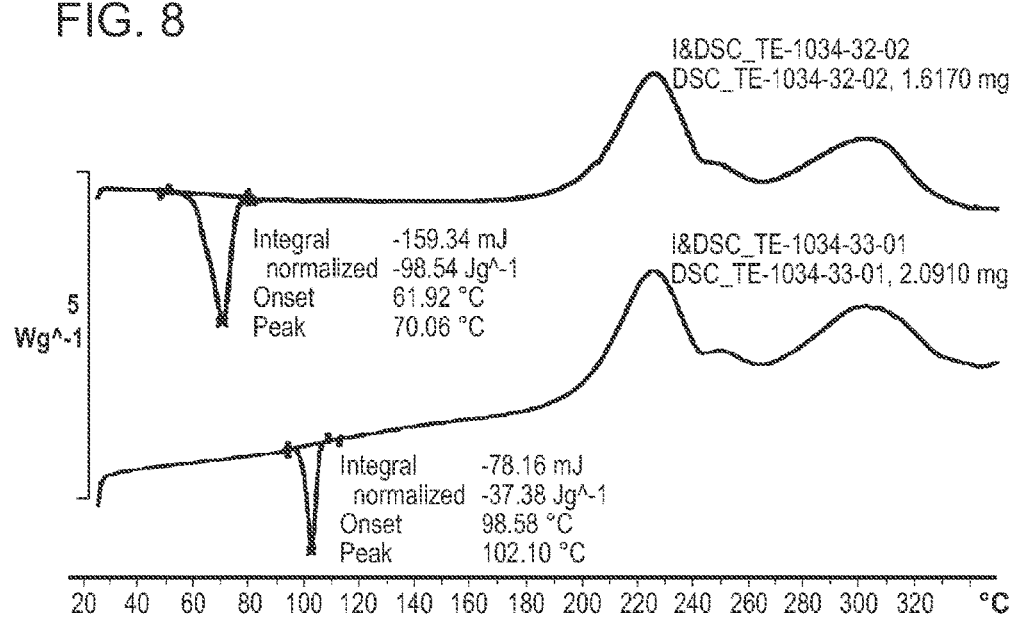
FIG. 8: depicts thermal analysis patterns of X-hydrate (upper) and anhydrous (lower) forms of compound 1.

What is claimed:

1. A 1.5 hydrate polymorph of a compound of formula 1,

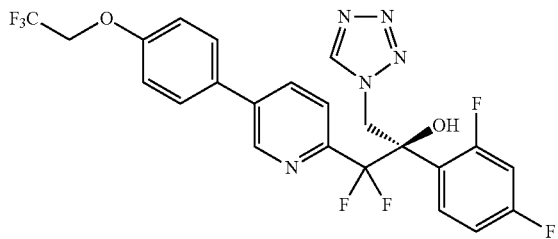 [SMILES: O[C@@](Cn1cnnn1)(c1ccc(F)cc1F)C(F)(F)c1ccc(-c2ccc(OCC(F)(F)F)cc2)cn1]

characterized by at least one of:
(i) a powdered X-ray diffraction pattern having two or more peaks expressed in degrees 2-theta±0.2° and selected from peaks delineated in the pattern of FIG. 5; or
(ii) a DSC thermogram showing an endotherm at about 85° C.

2. A process to prepare a 1.5 hydrate polymorph of compound 1:

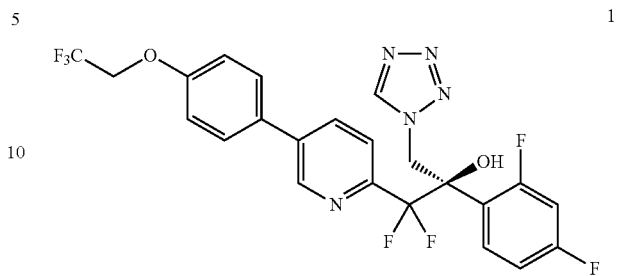

comprising suspending a compound of formula 1 in a solvent and isolating any solid material.

3. The compound of claim 1, characterized by a powdered X-ray diffraction pattern having peaks expressed in degrees 2-theta±0.2° at each of about 7.9, 8.9, 16.2, 22.6, 24.2, 26.6, 28.0.

4. The compound of claim 1, wherein the compound is essentially solvent free.

5. The compound of claim 1, wherein the compound has 0.1-0.5% weight solvent.

6. The process of claim 2, wherein the compound suspended in the solvent is in one of an amorphous, solvate, or hydrate form.

7. The process of claim 2, wherein the solvent is an organic solvent.

8. The process of claim 2, wherein the solvent is a $C_3$-$C_{10}$ alcohol.

9. The process of claim 2, comprising two or more solvents.

10. The process of claim 2, wherein one solvent is a $C_3$-$C_{10}$ alcohol and one solvent is water.

11. The process of claim 2, wherein the isolated solid material is dried at a temperature of 30-60° C.

* * * * *